United States Patent
Robbins et al.

(10) Patent No.: US 9,940,094 B1
(45) Date of Patent: Apr. 10, 2018

(54) DYNAMIC MUTING AUDIO TRANSDUCER CONTROL FOR WEARABLE PERSONAL COMMUNICATION NODES

(71) Applicant: Orion Labs, San Francisco, CA (US)

(72) Inventors: Jesse Robbins, San Francisco, CA (US); Greg Albrecht, San Francisco, CA (US); Ellen Juhlin, San Francisco, CA (US); Roger Wood, San Francisco, CA (US); Neil Girling, Oakland, CA (US)

(73) Assignee: ORION LABS, San Francisco, CA (US)

( * ) Notice: Subject to any disclaimer, the term of this patent is extended or adjusted under 35 U.S.C. 154(b) by 27 days.

(21) Appl. No.: 15/157,543

(22) Filed: May 18, 2016

Related U.S. Application Data (60) Provisional application No. 62/163,731, filed on May 19, 2015.

(51) Int. Cl.
| | |
|---|---|
| *H04M 1/00* | (2006.01) |
| *G06F 3/16* | (2006.01) |
| *H04B 1/3827* | (2015.01) |

(52) U.S. Cl.
CPC ............ *G06F 3/165* (2013.01); *H04B 1/385* (2013.01)

(58) Field of Classification Search
None
See application file for complete search history.

(56) References Cited

U.S. PATENT DOCUMENTS

| | | | |
|---|---|---|---|
| 2006/0276213 A1 | 12/2006 | Gottschalk et al. | |
| 2014/0229959 A1* | 8/2014 | Beckhardt | H04N 21/65 725/5 |
| 2015/0010169 A1* | 1/2015 | Popova | H04S 7/303 381/107 |
| 2015/0350027 A1* | 12/2015 | Raissinia | H04B 17/318 455/517 |

FOREIGN PATENT DOCUMENTS

EP         1921825 A1     5/2008

\* cited by examiner

*Primary Examiner* — Mohammed Rachedine (57) ABSTRACT

Systems, methods, software and apparatus that enable dynamic audio transducer control include obtaining attribute information relating to multiple communication nodes that are communication node group members. A group management system or other computing system receives attribute information from two or more of the communication nodes and determines settings for one or more audio transducers (e.g., speakers and microphones) in the group's communication nodes based on the attribute information. An audio transducer command is transmitted to or imposed on one or more of the nodes. Attribute information can include node attributes and/or changes to attributes. Audio transducer commands transmitted or otherwise imposed on nodes can include muting and unmuting commands, as well as setting volume levels and other audio settings associated with a node's operation.

18 Claims, 6 Drawing Sheets

DYNAMIC MUTING AUDIO TRANSDUCER CONTROL FOR WEARABLE PERSONAL COMMUNICATION NODES

RELATED APPLICATIONS

This application claims the benefit of, and priority to, U.S. Provisional Patent Application No. 62/163,731, entitled "DYNAMIC MUTING FOR WEARABLE PERSONAL COMMUNICATION NODES," filed May 19, 2015, and which is hereby incorporated by reference in its entirety for all purposes.

TECHNICAL FIELD

Aspects of the disclosure are related to communications and, in particular, to establishing, managing and maintaining communication groups based on attributes.

TECHNICAL BACKGROUND

Telephones, computers, and tablets provide an efficient way for users in different physical locations to communicate with one another. However, such devices often require the user to actively monitor conditions and to provide multiple inputs and preferences, including device-related audio transducer settings, for each of the communications before the communications can take place. Such audio transducer settings may be based on factors and conditions that are difficult, inconvenient, impractical or impossible for a user to actively monitor and adjust while actively communicating with member nodes in the group. Preferences may include the individuals involved in the communication group and contact identifiers for such individuals, among other preferences. Moreover, when busy performing other tasks and/or engaging in communications, it is often difficult to adjust the volume and/or other audio transducer settings in changing environments while physically holding a telephone, computer, or tablet, and distracts from the primary task.

Overview

Implementations of dynamic audio transducer control include obtaining (e.g., monitoring, collecting or receiving) attribute information relating to a plurality of communication nodes that are members of a defined communication node group. A group management system or other computing system receives attribute information from two or more of the communication nodes. Audio transducer settings for at least one of the communication nodes are determined based on the attribute information. An audio transducer command is then transmitted to or otherwise imposed on one or more of the communication nodes. The attribute information can include attributes and/or changes to attributes of the communication nodes, such as node location, noise level in a current environment, pre-determined noise level user preference(s), node proximity to other nodes, communication status, headphone or earpiece jack use, identity, and traveling speed. Audio transducers can include communication node speakers and microphones and commands transmitted or otherwise imposed on nodes can include muting and unmuting commands, as well as setting volume levels and other audio settings associated with a node's operation.

Implementations can be used to adjust audio transducer activation and deactivation based on changing group membership and locations during an ongoing communication session. Moreover, implementations can protect secure communications from inadvertent, accidental and other unwanted disclosure of communication content.

This Overview is provided to introduce a selection of concepts in a simplified form that are further described below in the Technical Disclosure. It may be understood that this Overview is not intended to identify or emphasize key features or essential features of the claimed subject matter, nor is it intended to be used to limit the scope of the claimed subject matter.

DETAILED DESCRIPTION

Figure 1:
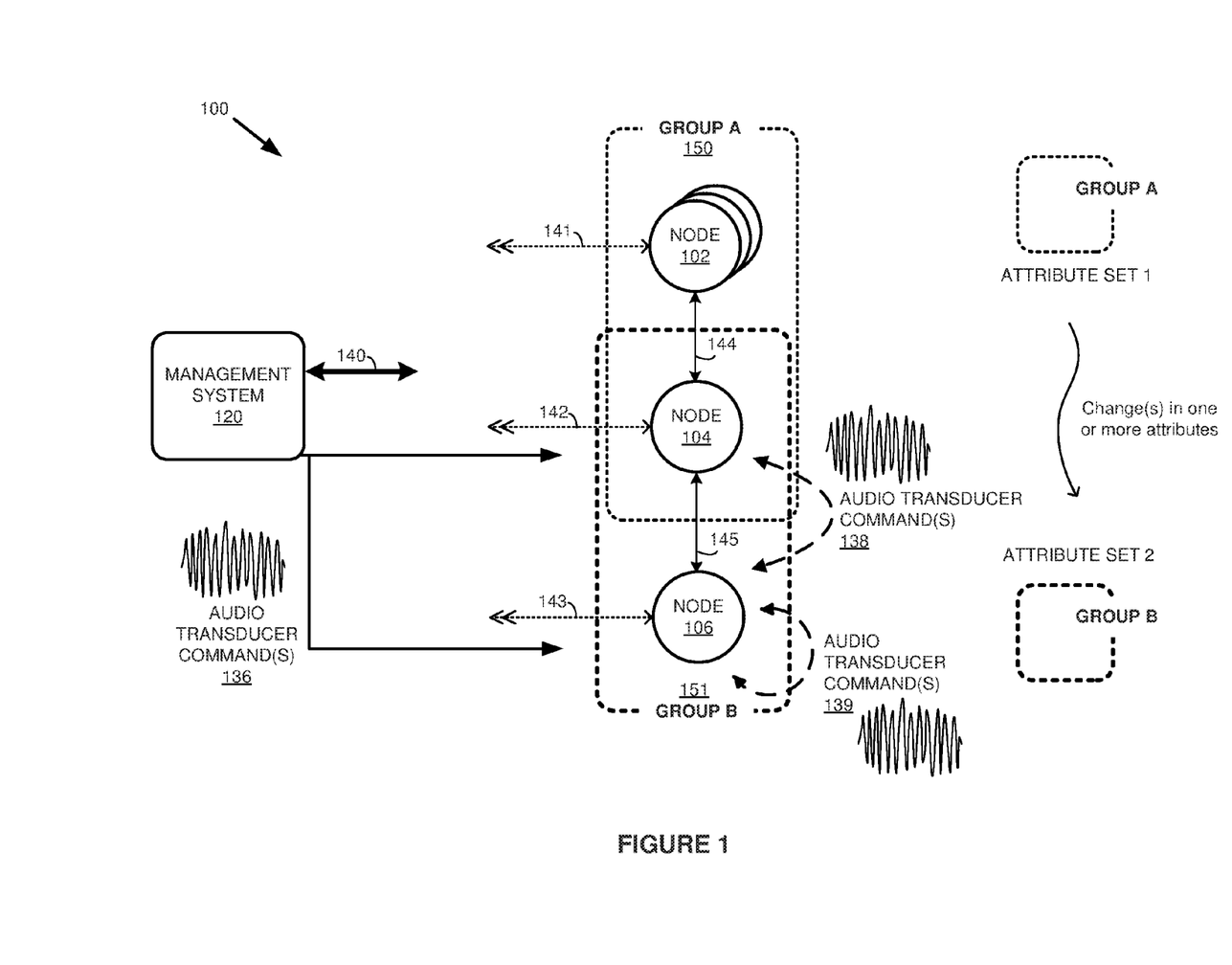
FIG. 1 illustrates a system and operation of dynamic audio transducer control across personal communication nodes.

FIG. 1 illustrates system 100 for dynamic audio transducer control (e.g., muting, unmuting, volume adjustment, and/or adjusting another audio transducer setting) across personal communication nodes 102-106. Dynamic audio transducer control such as dynamic muting automatically adjusts the audio transducer levels of personal communication nodes 102-106 without the need for user input. Audio transducers comprise audio input devices (capable of collecting and transmitting sound) and audio output devices (capable of broadcasting audio), such as speakers, microphones and other similar devices. Personal communication nodes 102-106 are able to independently adjust microphone and speaker muting. Audio transducers, as used herein, may interchangeably refer to one or more of an audio input device, such as a microphone, and/or an audio output device, such as a speaker.

In one non-limiting example of dynamic audio transducer control such as muting of personal communication nodes 102-106, audio transducers of personal communication nodes 102-106 autonomously and dynamically mute their audio transducers when two or more personal communication nodes are in close enough proximity that end users of the nearby nodes are within audible range of one another. Personal communication nodes 102-106 typically operate in groups, such as exemplary Group A 150 and Group B 151, which are dynamically defined and updated by management system 120 based on attributes communicated to management system 120 from personal communication nodes 102-106. Each of groups 150-151 comprises a nexus of specified personal communication nodes 102-106 for interactive communications, information sharing, data exchange, and other mutual exchange.

Personal communication nodes 102-106 may each comprise transceivers, audio transducers, processing systems, communication interfaces, environmental sensors, accelerometers, gyroscopes, Global Positioning System (GPS) receivers, user interfaces and other systems to detect and/or collect various attributes and to communicate with management system 120 and other personal communication nodes. Management system 120 may comprise a server system comprising one or more computing devices capable of managing services to a plurality of personal communication nodes, such as personal communication nodes 102-106. Management system 120 is capable of operating over one or more computing devices.

Personal communication nodes 102-106 communicate with each other or with other personal communication nodes over one or more of associated links 144-145. Personal communication nodes 102-106 can also communicate with management system 120 over associated ones of links 141-143. Management service system 120 communicates and personal communication nodes communication via link 140, which can comprise one or more network links in this example. Links 140-143 connect personal communication nodes 102-106 to management system 120 using Long Term Evolution (LTE), (GSM), CDMA, IEEE 802.11 WiFi, Bluetooth, Personal Area Networks (PANS), Wide Area Networks, (WANs), Local Area Networks (LANs), Wireless Local Area Networks (WLANS), Internet Protocol (IP), Ethernet, synchronous optical networking (SONET), hybrid fiber-coax (HFC), Time Division Multiplex (TDM), asynchronous transfer mode (ATM), circuit-switched, communication signaling, wireless communications, or some other communication format, including improvements thereof.

Communication links 144-145 connect personal communication nodes 102 and 104 and personal communication nodes 104 and 106, respectively, using Bluetooth. IEEE 802.11 WiFi, infrared, ultrasonic or any communication format including improvements thereof. Communication links 140-145 each use metal, glass, optical, air, space, or some other material as the transport media. Communication links 140-145 may each be a direct link, or may include intermediate networks, systems, or devices, and may include a logical network link transported over multiple physical links.

In FIG. 1, each personal communication node 102-106 obtains (e.g., monitors and/or collects) one or more attributes from associated audio transducers, GPS receivers, accelerometers, transceivers, sensors, or other devices capable of measuring, calculating, collecting, monitoring, etc. the attributes discussed herein. These attributes comprise any data or other information that may be used for dynamic audio transducer control such as muting, unmuting and other audio transducer settings control across personal communication nodes 102-106. For example, the noise level (volume) present in an environment, pre-determined noise level (volume) preference of a user, proximity of one personal communication node 102-106 to another, location, communication status, identity, and traveling speed are non-limiting examples of attributes of personal communication nodes 102-106 that may be used for dynamic muting across personal communication nodes 102-106.

Personal communication nodes 102-106 periodically send messages to management system 1:20 (e.g., by transferring such messages for delivery to system 120) indicating attribute changes (e.g., at least dynamic changes). Personal communication nodes 102-106 may send a message to management system 120 whenever an attribute changes and/or at periodic intervals. Management system 120 uses attribute changes to create, modify and/or disband groups of personal communication nodes 102-106 and for dynamic audio transducer control (e.g., muting, unmuting, volume adjustment, and/or adjusting another audio transducer setting) across personal communication nodes 102-106.

In the non-limiting example of FIG. 1, management system 120 forms Group A 150 to include personal communication nodes 102 and 104 based on Attribute Set 1, Personal communication nodes 102 and 104 communicate with each other either via links 141 and 142 and/or via link 144. Management system 120 determines that personal communication nodes 102 and 104 of Group A 150 are outside audible range (i.e., the nodes' users are not close enough for normal conversational communication) based on Attribute Set 1 and the audio transducers of personal communication nodes 102 and 104 are automatically adjusted to desirable levels (e.g., depending upon environmental noise and/or other conditions).

Based on Attribute Set 2, which represents updated attributes and/or changes to one or more attributes in Attribute Set 1 in the non-limiting example of FIG. 1, management system 120 forms Group B 151, which includes personal communication nodes 104 and 106. Personal communication nodes 104 and 106 communicate with each other either via links 142 and 143 and/or via link 145. Personal communication node 104 is a member of both preceding Group A 105 and subsequent Group B 151. In the non-limiting example of FIG. 1, Attribute Set 2 indicates that the users of nodes 104 and 106 of Group B 151 are within conversational (audible) range of one another, so management system 120 transfers an audio transducer command 136 to mute personal communication devices 104 and 106 by disabling their respective audio transducers. In implementations where communication nodes monitor and determine audio transducer settings within a node group, audio transducer commands can be sent directly between nodes (e.g., as seen with regard to command(s) 138 of FIG. 1) and/or can be self-imposed (e.g., as seen with regard to command(s) 139 of FIG. 1).

During operation, any of personal communication nodes 102-106 can detect changes in one or more attributes and transfer messages for delivery to management system 120 indicating such changes (e.g., at least dynamic changes in the one or more attributes). Management system 120 modifies the group membership status of personal communication nodes 102-106 and dynamic audio transducer control (e.g., muting, unmuting, volume adjustment, and/or adjusting another audio transducer setting) across personal communication devices 102-106 using such attribute change information (e.g., at least the dynamic changes in one or more attributes).

In an alternative non-limiting example of FIG. 1, for example where nodes 104 and 106 communicate directly with one another using link 145, the communication nodes 104, 106 may share attribute information with one another. When one or both of communication nodes 104, 106 determine (based on attribute information received from the other communication node) that they are with audible range, then one or both of the communication nodes 104, 106 can send an audio transducer command to the other communication node to instruct it to mute one or more audio transducers. The attribute information and commands shared in such a direct exchange between personal communication nodes can also be shared with management system 120 so that its information about Group B 151 is up to date and so that management system 120 itself can issue audio transducer and/or other commands and messages relating to Group B 151.

Figure 2:
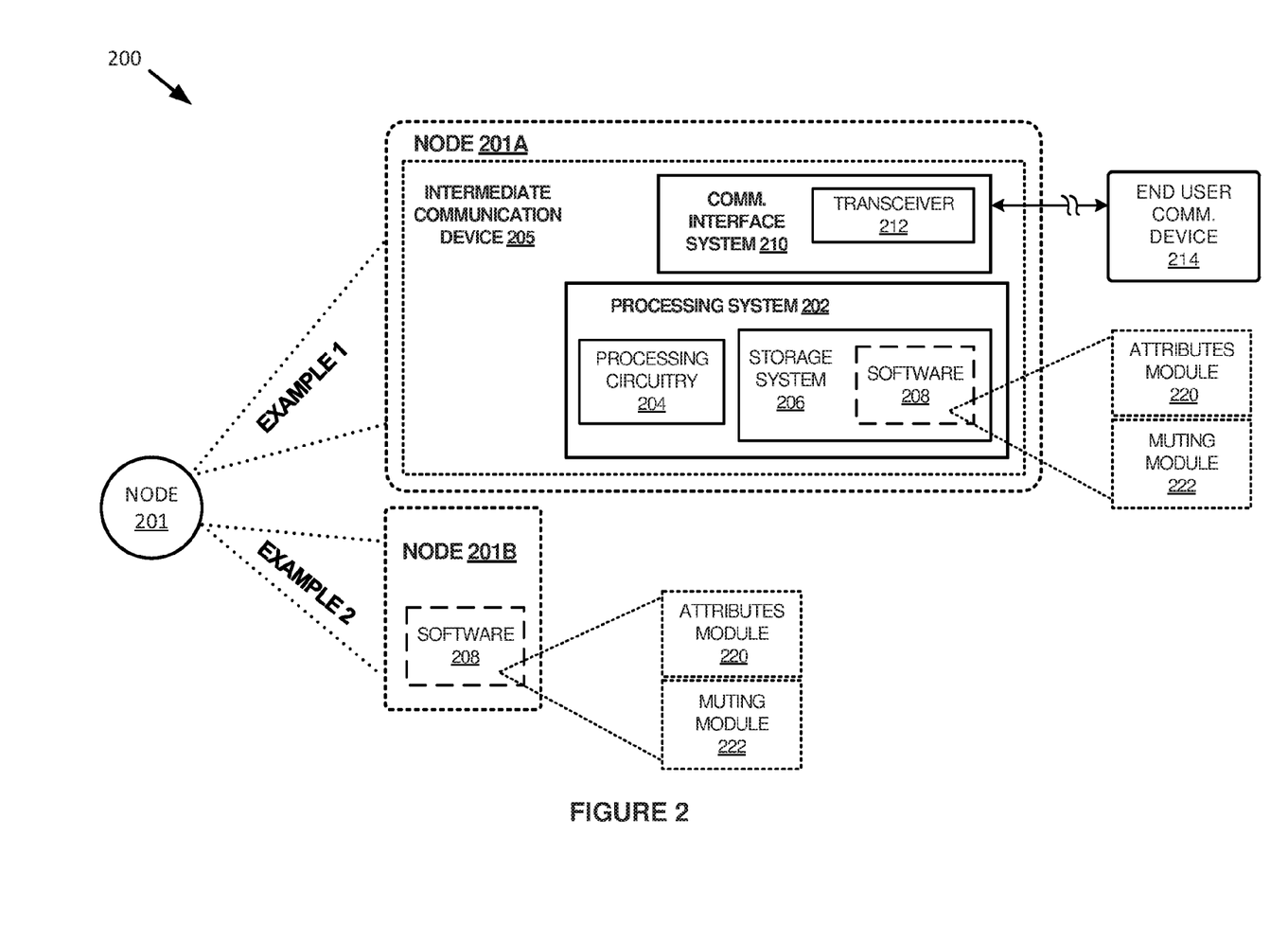
FIG. 2 illustrates exemplary systems for personal communication nodes.

To further illustrate exemplary implementations for dynamic audio transducer control (e.g., muting, unmuting, volume adjustment, and/or adjusting another audio transducer setting) across personal communication nodes and configurations of the personal communication nodes of FIG. 1, node 201 of FIG. 2 is presented (node 201 may represent one of the communication nodes 102-106 of FIG. 1 or another alternate communication node implementation). A first non-limiting example (Example 1) illustrates a personal communication node 201A comprising a separate end user device that communicates with other group members via an intermediate communication device (e.g., a wireless communication device) In some implementations, the end user device can be a personal (e.g., wearable) electronic device that communicates through an intermediate communication device such as a smartphone, tablet, laptop or other computing system or device.

A second non-limiting example (Example 2) illustrates a personal communication node 201B that does not employ multiple distinct devices, but instead utilizes a single wireless communication device, such as a personal communication node that contains and includes all necessary wireless communication interfaces and processing resources, among other features. Furthermore, software 208 usable in these and other examples can comprise a virtual machine that is executed on a computing device, including virtual devices or software executed by a virtualized processing system or virtualized computing system. It should be understood that features and functions of management system 120 of FIG. 1 can be included in the non-limiting examples of FIG. 2, along with features and functions of the personal communication nodes.

As noted, FIG. 2 illustrates two non-limiting exemplary systems 200 for personal communication nodes, such as personal communication node 201. Personal communication node 201 can be an example of personal communication nodes 102-106; however, personal communication node 201 may have alternative configurations and methods of operation. Example 1 comprises node 201A, which includes intermediate wireless communication device 205 and end user device 214. Intermediate communication device 205 may be a wireless device that comprises a smartphone, tablet device, computer, gaming device, laptop computer, or some other communication device capable of communicating using packet networks or some other communication network. Example 2 illustrates personal communication node software within an operating environment of an electronic device, wherein the electronic device may comprise a smartphone, tablet device, computer, gaining device, laptop computer, or some other communication device capable of communicating using packet networks or some other communication network, running a personal communication node software application that comprises personal communication node 201.

In the illustrated Example 1, node 201A further comprises processing system 202 and communication interface system 210. Processing system 202 further comprises processing circuitry 204 and storage system 206. Processing circuitry 204 comprises microprocessors and other circuitry that retrieves and executes software 208 from storage system 206. Processing circuitry 204 may be embedded in various types of equipment and may comprise a single device or could be distributed across multiple devices—including devices in different geographic areas.

Storage system 206 comprises a non-transitory computer readable storage medium, such as a disk drive, flash drive, data storage circuitry, or some other hardware memory apparatus. Storage system 206 may comprise a single device or could be distributed across multiple devices—including devices in different geographic areas. Storage system 206 may be embedded in various types of equipment. In some examples, a computer apparatus and/or computing system could comprise processing circuitry 204, storage system 206 and software 208. Software 208 comprises attributes module 220 and audio transducer control module 222, which may be part of or supplemental to communication software that enables group members' communication with one another. In addition, software 208 may include operating systems, utilities, drivers, network interfaces, applications, or some other type of software.

Attributes module 200 obtains (e.g., monitors, collects and/or stores) one or more attributes of personal communication node 201A and periodically transfers a message for delivery to a management system, where the message includes attribute information (e.g., regarding changes in the one or more attributes, and/or providing at least dynamic changes). Personal communication node 201A may comprise attribute sensors such as transceivers, speakers, microphones, processing systems, communication interfaces, environmental sensors, accelerometers, gyroscopes, Global Positioning System (GPS) receivers, user interfaces and other systems to monitor various attributes and provide communications to a management system (e.g., management system 120 of FIG. 1). Attributes module 220 may monitor attribute sensors (e.g., periodically or continuously) or attribute sensors may send an interrupt to attributes module 200 when a change is detected. Audio transducer control module 222 receives audio transducer commands transferred by a management system or the like (or, in some implementations, commands from other nodes or commands that are self-imposed), and enables, adjusts or disables one or more audio transducers of personal communication node 201A based at least on attributes monitored by personal communication node 201A.

Communication interface system 210 further comprises transceiver 212 for communicating with device 214. Transceiver 212 comprises communication components, such as ports, signal processing circuitry, memory, software, and the like. Transceiver 212 communicates with device 214 over a link that may comprise a Bluetooth communication link, WiFi link, infrared, ultrasonic or any other communication link between personal communication node 201A and device 214.

In the illustrated Example 2, node 201B may comprise a processing system further comprising processing circuitry and a storage system. Processing circuitry may comprise microprocessors and other circuitry that retrieves and executes software 208. Processing circuitry may comprise a single device or could be distributed across multiple devices—including devices in different geographic areas. Processing circuitry may be embedded in various types of equipment. Node 201B may also comprise a storage system further comprising a non-transitory computer readable storage medium, such as a disk drive, flash drive, data storage circuitry, or some other hardware memory apparatus. The storage system may comprise a single device or be distributed across multiple devices—including devices in different geographic areas. The storage system may be embedded in various types of equipment.

Node 201B further comprises software 208 including attributes module 220 and audio transducer control module 222, which may be part of or supplemental to communication software that enables group members' communication with one another. In addition, software 208 may include operating systems, utilities, drivers, network interfaces, applications, or some other type of software. Attributes module 220 monitors one or more attributes of personal communication node 201B and periodically transfers a message for delivery to a management system (e.g., indicating at least dynamic changes in the one or more attributes). Audio transducer control module 222 receives audio transducer control commands transferred by the management system, and enables, adjusts or disables the audio transducers of personal communication node 201B based at least on attributes obtained (e.g., monitored and/or collected) by node 201B. Speakers and microphones may be muted, adjusted, etc. separately in some implementations.

Figure 3:
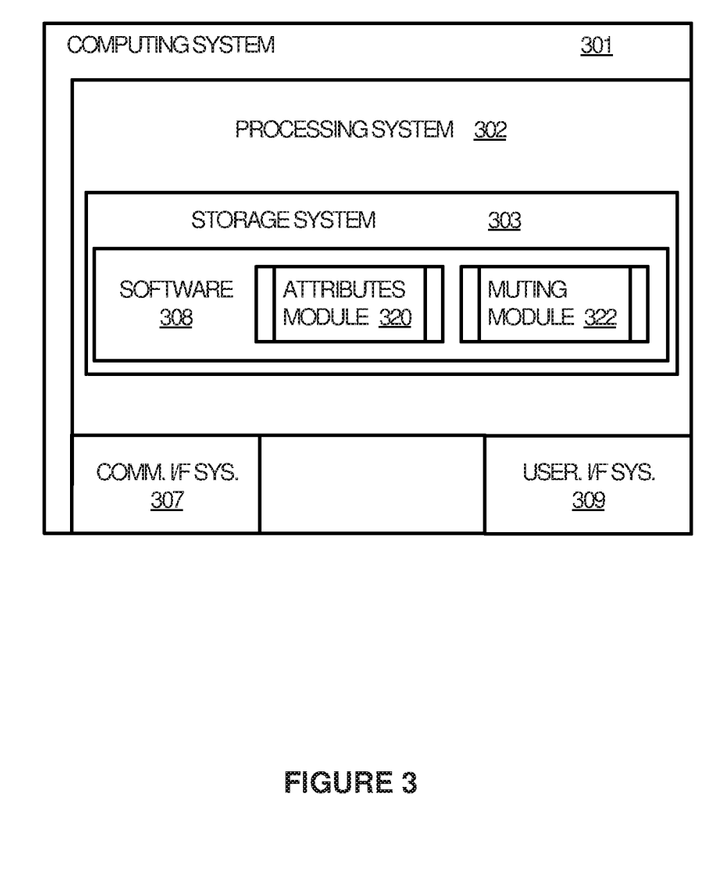
FIG. 3 illustrates a system for dynamic audio transducer control across personal communication nodes and/or a management system.

FIG. 3 illustrates a system for dynamic audio transducer control (e.g., muting, unmuting, volume adjustment) across personal communication nodes or a management system. Referring to FIG. 3, computing system 301 is generally intended to represent one or more computing systems on which software 308 may be deployed and executed in order to implement attributes module 320 and audio transducer control module 322 to operate as a personal communication node or a management system. In the non-limiting exemplary system 301 of FIG. 3, software 308 and any other software usable to implement dynamic audio transducer control (e.g., muting, unmuting, volume adjustment) as described herein can be stored in storage system 303, which is part of processing system 302, though other configurations can be used. Moreover, computing system 301 may also be suitable as any computing system on which software 308 may be staged and from where one or both may be distributed, transported, downloaded, or otherwise provided to yet another computing system for deployment and execution, or yet additional distribution.

Communication interface system 307 may include communication connections and devices that allow for communication with other computing systems over a communication network. Examples of connections and devices that together allow for inter-system communication may include network interface cards, antennas, power amplifiers, RF circuitry, transceivers, and other communication circuitry. The connections and devices may communicate over communication media to exchange communications with other computing systems or networks of systems, such as metal, glass, air, or any other suitable communication media. The aforementioned media, connections, and devices are well known and need not be discussed at length here.

User interface system 309 is optional and may include a keyboard, a mouse, a voice input device, a touch input device for receiving a touch gesture from a user, a motion input device for detecting non-touch gestures and other motions by a user, and other comparable input devices and associated processing elements capable of receiving user input from a user. Output devices such as a display, speakers, haptic devices, and other types of output devices may also be included in user interface system 309. In some cases, the input and output devices may be combined in a single device, such as a display capable of displaying images and receiving touch gestures. The aforementioned user input and output devices are well known in the art and need not be discussed at length here.

User interface system 309 may also include associated user interface software executable by processing system 302 in support of the various user input and output devices discussed above. Separately or in conjunction with each other and other hardware and software elements, the user interface software and user interface devices may support a graphical user interface, a natural user interface, or any other type of user interface. In addition, user input made with respect to the user interfaces may be input via user interface system 309.

Communication between computing system 301 and any other computing system may occur over a communication network or networks and in accordance with various communication protocols, combinations of protocols, or variations thereof. Examples of such communication networks include intranets, internets, the Internet, local area networks, wide area networks, wireless networks, wired networks, virtual networks, software defined networks, data center buses, computing backplanes, or any other type of network, combination of network, and/or variations thereof and other well known modes. Some communication protocols that may be used include, but are not limited to, the Internet protocol (IP, IPv4, IPv6, etc.), the transfer control protocol (TCP), and the user datagram protocol (UDP), as well as any other suitable communication protocol, variation, or combination thereof.

In any of the aforementioned examples in which information is exchanged, the exchange of information may occur in accordance with any of a variety of protocols, including FTP (file transfer protocol), HTTP (hypertext transfer protocol), HTTPS (HTTP secure), SOAP (simply object access protocol), REST (representational state transfer), WebSocket, DOM (Document Object Model), HTML (hypertext markup language), CSS (cascading style sheets), HTML5, XML (extensible markup language), JavaScript, JSON (JavaScript Object Notation), and AJAX (Asynchronous JavaScript and XML), as well as any other suitable protocol, variation, or combination thereof.

Figure 4A:
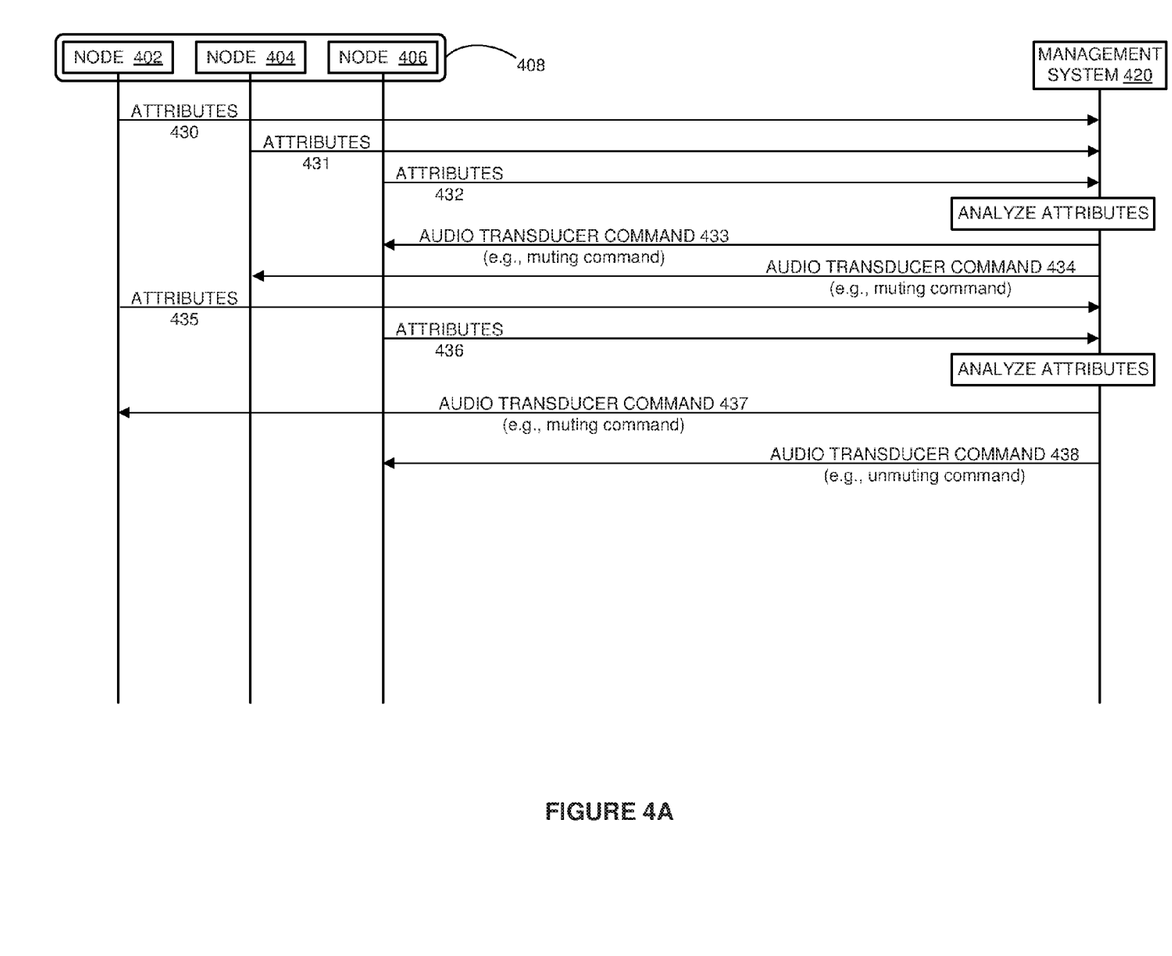
FIG. 4A illustrates operation of dynamic audio transducer control across personal communication nodes.

FIG. 4A illustrates the operation of dynamic audio transducer control (e.g., muting, unmuting, volume adjustment) across personal communication nodes 402-406 and management system 420. Personal communication nodes 402-406 are examples of personal communication nodes 102-106 and personal communication node 201; however personal communication nodes 401-406 may have alternative configurations and methods of operation. Likewise, management system 420 is an example of management system 120; however management system 420 may have alternative configurations and methods of operation.

In this non-limiting example the management system 420 receives attribute information and bases audio transducer control commands issued to various personal communication nodes 402-406 that are members of a communication node group 408. Personal communication node 402 transfers attribute information (430) to management system 420, where the attribute information can comprise one or more attributes and/or attribute changes. Similarly, personal communication node 404 transfers attribute information (431) to management system 420 and personal communication node 406 transfers attribute information (432) to management system 420. Management system 420 receives the attribute information from personal communication nodes 402-406, analyzes the attribute information, and, based on the attribute information, decides to issue an audio transducer command to mute the audio transducers of personal communication nodes 404 and 406.

Management system 420 transfers a muting command (audio transducer command 433) to personal communication node 404 and transfers a muting command (audio transducer command 434) to personal communication node 406 (in some implementations commands 432 and 433 may be combined into a single command issued to all affected personal communication nodes). Personal communication nodes 404 and 406 receive the muting command(s) from management 420 and responsively mute their respective audio transducers as instructed. Personal communication node 402 then senses a change in one or more attributes and transfers associated attribute information (435) to management system 420. Personal communication node 406 likewise senses a change in one or more attributes and transfers the associated attribute information (436) to management system 420. Management system 420 receives the attribute information from personal communication nodes 402 and 406, analyzes the attribute information, and determines to mute the audio transducers of personal communication node 402 and unmute the audio transducers of personal communication node 406. Management system 420 transfers a muting command (audio transducer command 437) to personal communication node 402. Personal communication node 402 receives the muting command and responsively mutes its audio transducers. Management system 420 sends an unmuting command (audio transducer command 438) to personal communication node 406. Personal communication node 406 receives the unmuting command and responsively enables one or more audio transducers, in some implementations adjusting the audio transducers to desirable operating levels depending upon the environment.

Figure 4B:
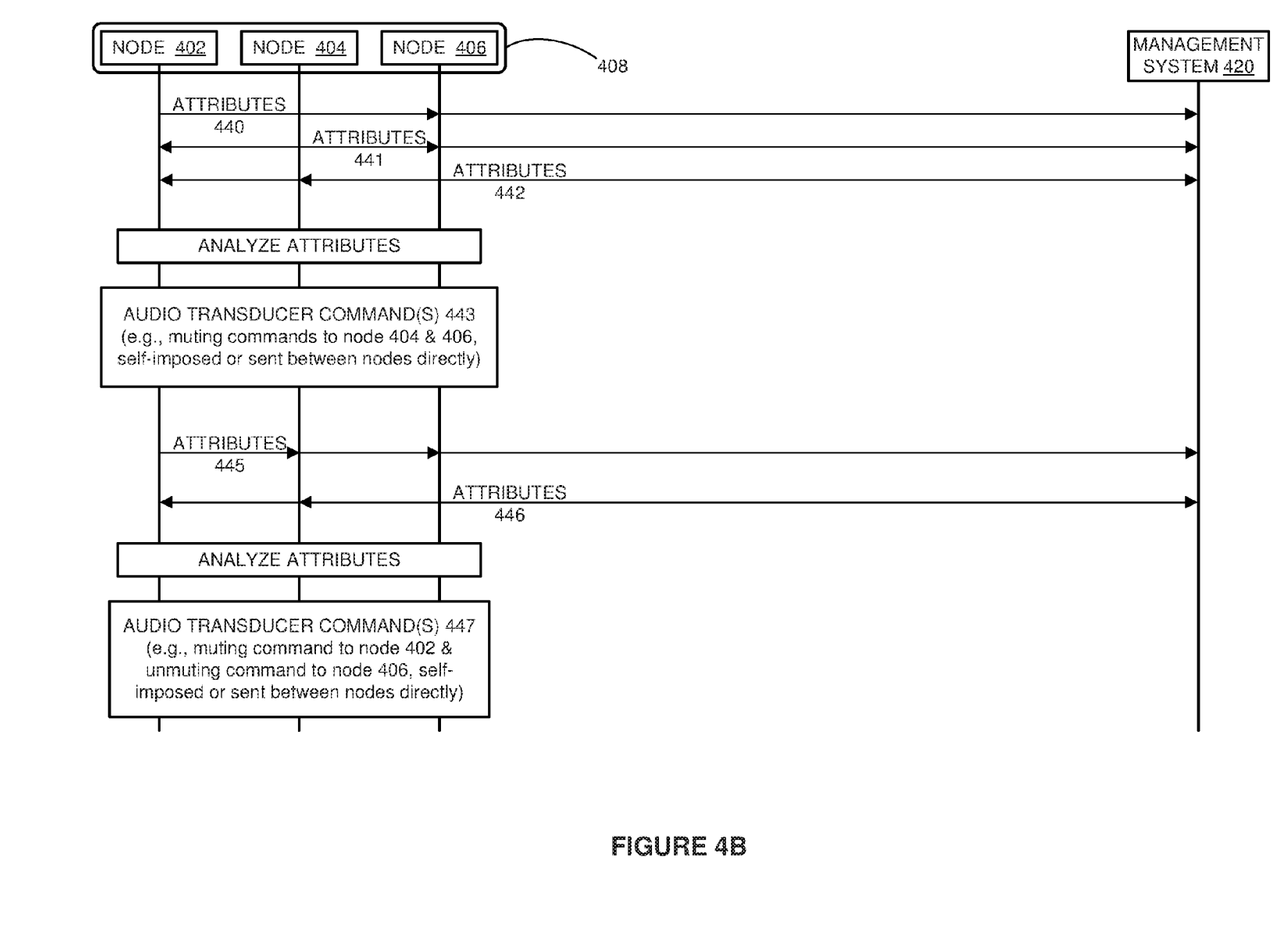
FIG. 4B illustrates operation of dynamic audio transducer control across personal communication nodes.

FIG. 4B provides another non-limiting example of dynamic audio transducer control using the same basic attribute information scenario as FIG. 4A. In the exemplary process of FIG. 4B, however, the personal communication nodes 402-406 are in direct communication with one another. This includes each personal communication node receiving attribute information from other personal communication nodes in the same group 408 and determining whether audio transducer changes are appropriate. Moreover, the nodes 402-406 are configured to analyze and impose audio transducer commands based on dynamic audio transducer controls (e.g., via communication software executed in each node 402-406).

In this non-limiting example the nodes 402-406 transmit attribute information to one another as well as the management system 420. Each node 402-406 can then base audio transducer control commands on attribute information shared among members of group 408. Personal communication node 402 transfers attribute information (440) to the other members of group 408 (and optionally to management system 420 to enable monitoring of status and other functions by the management system 420), where the attribute information can comprise one or more attributes and/or attribute changes. Similarly, personal communication node 404 transfers attribute information (441) to the other members of group 408 (and optionally to management system 420) and personal communication node 406 transfers attribute information (442) to the other members of group 408 (and optionally to management system 420). One or more of nodes 402-406 receive the attribute information from fellow group 408 members, analyze the attribute information, and, based on the attribute information, decide to impose (e.g., through self-imposition or direct communication with other group 408 member nodes) one or more audio transducer commands (443), for example muting the audio transducers of personal communication nodes 404 and 406, which then responsively mute their respective audio transducers as instructed.

Personal communication node 402 then senses a change in one or more attributes and transfers associated attribute information (445) to fellow group 408 member nodes (and optionally to management system 420). Personal communication node 406 likewise senses a change in one or more attributes and transfers the associated attribute information (446) to fellow group 408 members (and optionally to management system 420). One or more of the group 408 members receive the attribute information from nodes 402 and 406, analyze the attribute information, and determine to mute the audio transducers of personal communication node 402 and unmute the audio transducers of personal communication node 406. A muting command (e.g., part of audio transducer command 447) is then imposed on personal communication node 402, which responsively mutes its audio transducers. An unmuting command (e.g., part of audio transducer command 447) is imposed on personal communication node 406, which responsively enables one or more audio transducers, in some implementations adjusting the audio transducers to desirable operating levels depending upon the environment.

To provide a real-world example of operations similar to those described in connection with FIG. 4A above, the end users of personal communication nodes 402-406 might comprise people having a meeting. The end users of personal communication nodes 404 and 406 are in a conference room, while the end user of personal communication node 402 is heading to the conference room. Personal communication node 402 sends one or more attributes (430) to management system 420 indicating that it is not within audible range of personal communication nodes 404 and 406. Personal communication node 404 sends one or more attributes (431) to management system 420 indicating that personal communication node 404 is not within audible range of personal communication node 402, but is within audible range of personal communication node 406. Likewise, personal communication node 406 sends one or more attributes (432) to management system 420 indicating that personal communication node 406 is not within audible range of personal communication node 402 and is within audible range of personal communication node 404.

Management system 420 analyzes the attributes and determines to mute the speakers of personal communication nodes 404 and 406. The microphones of personal communication nodes 404 and 406 are not muted so that personal communication node 402 can receive audio from personal communication nodes 404 and 406. Management system 420 sends a muting command (433) to personal communication node 406 instructing it to mute the speaker. Likewise, management system 420 sends a muting command (434) to personal communication node 404 instructing it to mute the speaker. The end user of personal communication node 402 enters the conference room and personal communication node 402 sends one or more attributes (435) to management system 420 indicating that personal communication node 402 is within audible range of personal communication node 404. At the same time the end user of personal communication node 406 leaves the conference room and personal communication node 406 sends one or more attributes (436) to management system 420 indicating that personal communication node 406 is no longer within audible range of personal communication nodes 402 and 404. Management system 420 receives the attributes, analyzes the attributes and sends a muting command (437) to personal communication node 402 instructing it to mute the speaker. Personal communication node 402 receives the muting command and responsively mutes the speaker, but not the microphone. Management system 420 also sends an unmuting command (438) to personal communication node 406 instructing it to unmute the audio transducers. Personal communication node 406 receives the unmuting command and automatically adjusts the audio transducers to desirable levels based on the operating environment.

In other examples of the operations described above and illustrated in FIG. 4A, the end user of personal communication node 402 could be a designated speaker giving a lecture. In this case personal communication node 402 may leave the audio transducers active so that the speaker of personal communication node 402 can act to amplify the speaker's voice. The speakers of personal communication nodes 404 and 406 are off in this example, but the microphones remain on to capture the lecture. Also in this example, the microphones may use echo cancellation, directionality detection and other features that may or may not be included in the available audio transducer controls for nodes 402-406.

Figure 5:
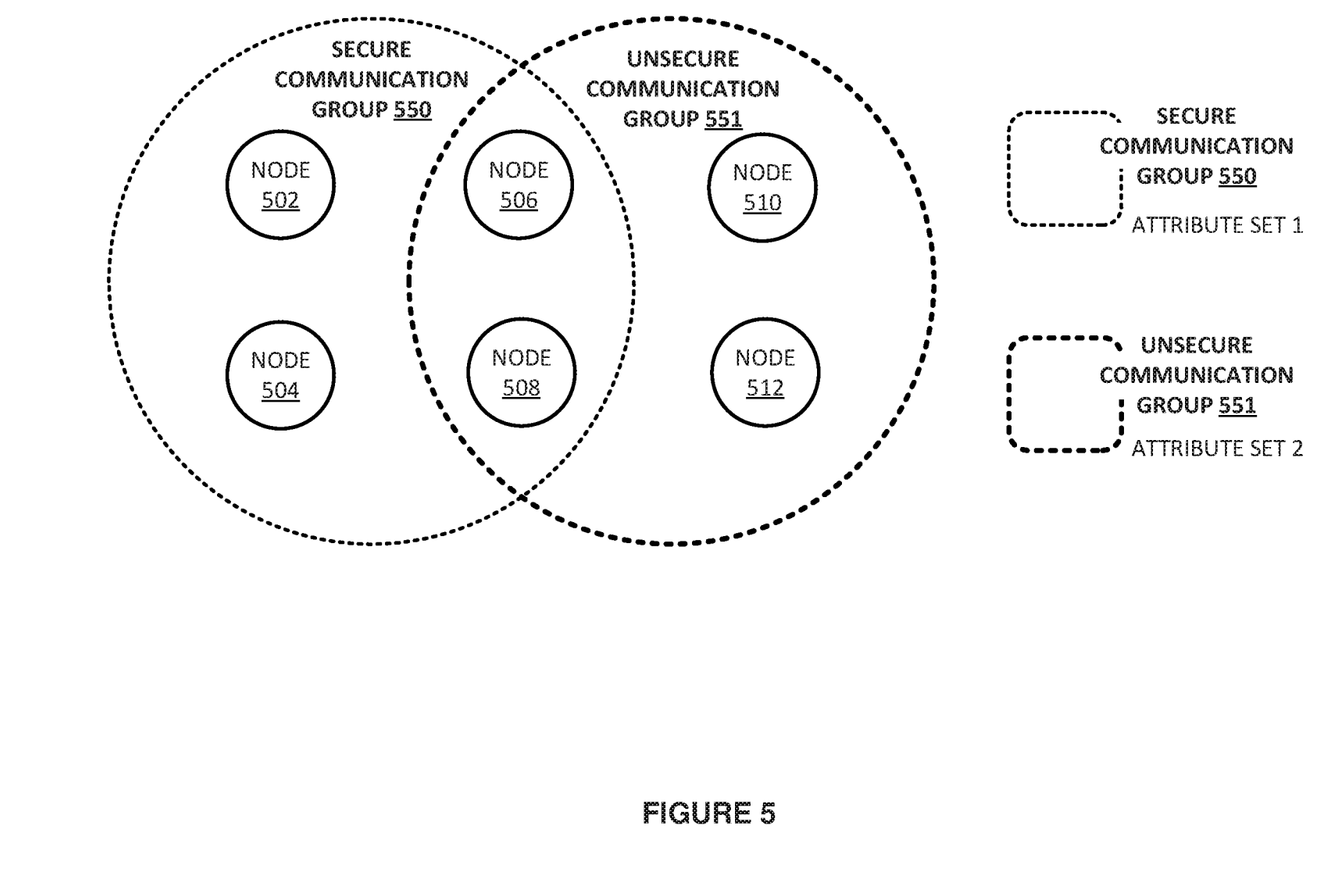
FIG. 5 illustrates dynamic audio transducer control across personal communication nodes operating in secured and unsecured communication groups.

FIG. 5 illustrates dynamic muting across personal communication nodes 502-512 operating in secured and unsecured communication groups. Personal communication nodes 502-512 are examples of personal communication nodes 102-106, personal communication node 201 and personal communication nodes 402-406; however, personal communication nodes 502-512 may have alternative configurations and methods of operation.

Personal communication nodes within a group may use secure communication methods. Secure communication methods include means by which users of personal communication nodes may securely share information among each other without third-party interception or monitoring of the information or associated communications. Secure communication methods may comprise symmetric key encryption, asymmetric key encryption, public-key encryption, or some other type of encryption, including combinations thereof. The actual communications between personal communication nodes can employ secure communication methods, and the associated links can employ secure communication methods independently. Secure communication group 550 comprises personal communication nodes 502-508 based at least upon Attribute Set 1. Unsecure communication group 551 comprises personal communication nodes 506-512 based at least upon Attribute Set 2. Personal communication nodes 506 and 508 belong to both secure communication group 550 and unsecure communication group 551.

Personal communication nodes 502-508 are able to communicate within secure communication group 550. Personal communication nodes 506-512 are able to communicate within unsecure communication group 551. Personal communication nodes 506 and 508 are members of both secure communication group 550 and unsecure communication group 551.

In one non-limiting example, if personal communication node 506 is communicating with other personal communication nodes within secure communication group 550 and comes within audible range of one or more personal communication devices belonging to unsecure communication group 551, then one or more audio transducers of personal communication node 506 can be muted to prevent a member of unsecure communication group 551 from hearing communication within secure communication group 550. The audio transducers are active when personal communication nodes 506 and 508 are communicating within secure communication group 550, but unsecure communication group 551 does not receive communications from personal communication nodes 506-508 intended for secure communication group 550 and vice-versa. This provides an example of software muting. The audio transducers are functioning, but a muting module within software (e.g., executed in each communication node and/or the management system) will prevent muted messages from being transferred to personal communication nodes outside the group.

Alternatively, personal communication nodes 506 and 508 may automatically mute the speakers when connected to headphones or an earpiece, thereby keeping the communications of secure communications group 550 private. In such examples, use of a headphone/earpiece jack on a device that is part of a personal communication node can be part of the attribute information shared with a management system and/or other group member nodes.

In another example, personal communication nodes 502-508 may automatically enter into a secure communication mode when a headset or earpiece is connected and automatically enter into an unsecure communication mode when the headset or earpiece is disconnected. Also, the end users of personal communication nodes 502-508 within secure communication group 550 might all use headsets or earpieces when they are not in the same room, but when they do meet in the same room personal communication nodes 502-508 may turn the speakers on. If the end user of personal communication node 508 leaves the room, the speaker may automatically mute and only allow communications to be received via a headset or earpiece.

In any of the aforementioned examples in which information is exchanged, the exchange of information may occur in accordance with any of a variety of protocols, including FTP (file transfer protocol), HTTP (hypertext transfer protocol), HTTPS (HTTP secure), SOAP (simply object access protocol), REST (representational state transfer), WebSocket, DOM (Document Object Model), HTML (hypertext markup language), CSS (cascading style sheets), HTML5, XML (extensible markup language), JavaScript, JSON (JavaScript Object Notation), and AJAX (Asynchronous JavaScript and XML), as well as any other suitable protocol, variation, or combination thereof.

While the Figures generally depict relatively few personal communication nodes, management systems and attribute sets, it may be appreciated that the concepts disclosed herein may be applied at scale. For example, any group disclosed herein could be deployed in support of any number of personal communication nodes.

The included descriptions and figures depict specific embodiments to teach those skilled in the art how to make and use the best mode. For the purpose of teaching inventive principles, some conventional aspects have been simplified or omitted. Those skilled in the art will appreciate variations from these embodiments that fall within the scope of the invention. Those skilled in the art will also appreciate that the features described above may be combined in various ways to form multiple embodiments. As a result, the invention is not limited to the specific embodiments described above, but only by the claims and their equivalents.

What is claimed is:

1. A method of operating a management system to manage the audio transducer status of a plurality of communication nodes comprising a first communication node and a second communication node, wherein each communication node comprises one or more audio transducers comprising a speaker and a microphone, the method comprising:
   a management system receiving attribute information from the first and second communication nodes, wherein the received attribute information comprises information about environmental noise levels and information about proximity of the first and second communication nodes;
   the management system determining muting/unmuting settings for at least one of the first and second communication nodes based on the received attribute information; and
   transmitting a muting/unmuting command to at least one of the first and second communication nodes based on the information about environmental noise levels and information about proximity of the first and second communication nodes.

2. The method of claim 1 wherein the attribute information further comprises information about the use of a headphone or earpiece jack.

3. The method of claim 1 wherein each communication node comprises two devices, wherein the two devices comprise a wireless intermediate communication device and an end user device linked to the intermediate communication device.

4. The method of claim 3 wherein the end user device comprises a wearable personal communication device wirelessly linked to the intermediate communication device, wherein the wearable personal communication device comprises the speaker and the microphone.

5. The method of claim 4 wherein the wireless intermediate communication device comprises one of the following:
   a smartphone;
   a tablet device;
   a gaming device; or
   a laptop.

6. The method of claim 1 wherein the attribute information further comprises changes in one or more communication node attributes.

7. The method of claim 1 wherein each communication node further comprises a computing system executing a communication software application.

8. A method of operating a management system to control a first communication node comprising two devices, wherein the two devices in the first communication node comprise a wireless intermediate communication device and a wearable end user device linked to the intermediate communication device, further wherein the wearable end user device comprises a speaker and a microphone, and wherein the first communication node is linked to a second communication node, the method comprising:
   the first communication node obtaining attribute information, wherein the attribute information comprises information about the following:
      proximity of the first communication node to the second communication node; and
      environmental noise levels;
   transmitting the attribute information to a management system;
   receiving a muting/unmuting command from the management system, wherein the muting/unmuting command is based on the attribute information; and
   responsive to the received muting/unmuting command, adjusting an audio transducer muting setting of the first communication node.

9. The method of claim 8 wherein the attribute information further comprises information about the use of a headphone or earpiece jack.

10. The method of claim 8 wherein the wireless intermediate communication device comprises one of the following:
    a smartphone;
    a tablet device;
    a gaming device; or
    a laptop.

11. The method of claim 8 wherein the attribute information further comprises changes in one or more communication node attributes.

12. The method of claim 8 wherein each communication node further comprises a computing system executing a communication software application.

13. A non-transitory computer readable storage medium having stored thereon program instructions to operate a group communication management system, including instructions, which when executed by one or more processors of a computing system, cause the computing system to:
    obtain attribute information relating to a plurality of communication nodes that are members of a communication node group, wherein each communication node comprises a speaker and a microphone, further wherein the received attribute information comprises information about the following:
       proximity of members of the plurality of communication nodes to one another; and
       environmental noise levels;
    determine one or more muting/unmuting settings for a first communication node in the plurality of communication nodes, wherein the one or more muting/unmuting settings is based on the received attribute information;
    impose at least one muting/unmuting setting command on the first communication node, wherein the at least one muting/unmuting setting command is based on the received attribute information and controls the muting status of the speaker and/or microphone of the first communication node.

14. The non-transitory computer readable storage medium of claim 13 wherein the first communication node comprising two devices, wherein the two devices in the first communication node comprise a wireless intermediate communication device and a wearable end user device linked to the intermediate communication device, further wherein the wearable end user device comprises the speaker and the microphone.

15. The non-transitory computer readable storage medium of claim 14 wherein the wireless intermediate communication device comprises one of the following:
    a smartphone;
    a tablet device;
    a gaming device; or
    a laptop.

16. The non-transitory computer readable storage medium of claim 13 wherein the attribute information further comprises information about the use of a headphone or earpiece jack.

17. The non-transitory computer readable storage medium of claim 13 wherein the attribute information further comprises changes in one or more communication node attributes.

18. The non-transitory computer readable storage medium of claim 13 wherein each communication node further comprises a computing system executing a communication software application.

* * * * *